(12) United States Patent
Rogowski et al.

(10) Patent No.: US 7,074,479 B2
(45) Date of Patent: Jul. 11, 2006

(54) SINTERED SHAPED BODY, WHOSE SURFACE COMPRISES A POROUS LAYER AND A METHOD FOR THE PRODUCTION THEREOF

(75) Inventors: Dirk Rogowski, Ebersbach a.d. Fils (DE); Hans-Georg Pfaff, Ostfildern (DE); Alwin Nagel, Aalen (DE)

(73) Assignee: Ceramtec AG Innovative Ceramic Engineering, Plochingen (DE)

( * ) Notice: Subject to any disclaimer, the term of this patent is extended or adjusted under 35 U.S.C. 154(b) by 0 days.

(21) Appl. No.: 10/240,177

(22) PCT Filed: Mar. 14, 2001

(86) PCT No.: PCT/EP01/02841

§ 371 (c)(1),
(2), (4) Date: Dec. 3, 2002

(87) PCT Pub. No.: WO01/72664

PCT Pub. Date: Oct. 4, 2001

(65) Prior Publication Data

US 2003/0180518 A1    Sep. 25, 2003

(30) Foreign Application Priority Data

Mar. 29, 2000 (DE) ................ 100 15 614

(51) Int. Cl.
*B32B 9/04* (2006.01)
*B32B 33/00* (2006.01)
*B05D 1/18* (2006.01)
*B05D 3/00* (2006.01)

(52) U.S. Cl. ................ 428/304.4; 428/316.6; 428/318.4; 428/318.6; 428/319.1; 428/332; 428/336; 427/372.2; 427/243; 427/343.2; 427/245; 427/299; 427/373; 427/429

(58) Field of Classification Search ............ 428/304.4, 428/318.4, 319.1, 318.6, 332, 336, 335, 220, 428/335.22; 427/2.1, 2.24, 2.26, 2.27, 2.29, 427/243, 244, 245, 247, 258, 260, 287, 261, 427/372.2, 373, 397.7, 421, 427, 429, 443.2, 427/299
See application file for complete search history.

(56) References Cited

U.S. PATENT DOCUMENTS 3,855,638 A * 12/1974 Pilliar .................. 623/23.55
5,240,480 A * 8/1993 Thorogood et al. ........... 96/4
5,866,245 A * 2/1999 Toriyama et al. ........ 428/319.3

FOREIGN PATENT DOCUMENTS

DE  26 20 694 A   11/1976
EP  0 328 041 A    8/1989
EP  0 832 865 A    4/1998

* cited by examiner

*Primary Examiner*—Stephen Stein
(74) *Attorney, Agent, or Firm*—Fulbright & Jaworski L.L.P.

(57) ABSTRACT

Porous coatings on high-performance ceramics attempt to combine the mechanical and thermal characteristics, which fulfil stringent demands, of the substrate material with the advantageous properties of coating materials. The subsequent application of layers of this type to the pre-sintered substrate produces unsatisfactory results in several areas of use with regard to possible layer thickness, porosity and adhesion. According to the invention, a shaped body consisting of a sintered, inorganic material, whose surface comprises a porous layer is produced in such a way that the base body is first formed as a green body. A layer in the form of a suspension, also containing an inorganic material, is then applied to the surface or to one section of the surface of the base body. A predetermined fraction of a pore-forming substance is mixed with at least the material of said layer and the green body with its applied layer is subjected to the thermal treatments required for producing a monolithic sintered body.

71 Claims, 2 Drawing Sheets

Figure 1:
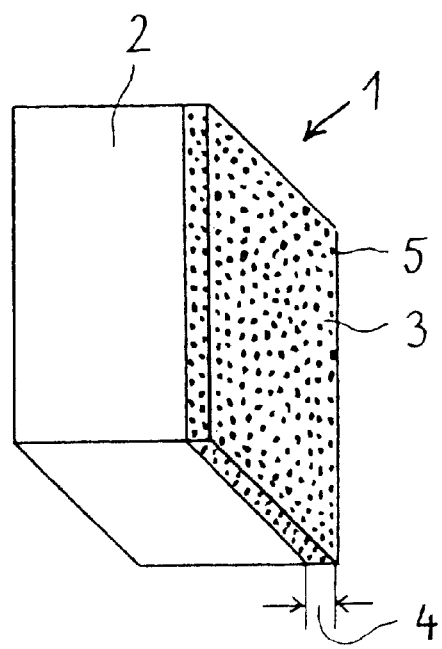

SINTERED SHAPED BODY, WHOSE SURFACE COMPRISES A POROUS LAYER AND A METHOD FOR THE PRODUCTION THEREOF

This is a 371 application of PCT/EP01/02841 filed Mar. 14, 2001 which claims priority to German Patent Application 100 15 614.2 filed Mar. 29, 2000.

The invention relates to a shaped body according to the preamble of the first claim, and to a method for the production of a shaped body corresponding to the sixteenth claim.

Coatings serve to improve mechanical, electrical, chemical, optical or other material properties on the surface of a component, in order to achieve application advantages, or to prevent or retard negative effects on the component in its use.

The application of dense coatings in the form of glazes on ceramic substrates has long been known. The substrate materials are mostly coarse or refractory ceramics with a correspondingly low level of mechanical properties and structure. The dense coating is intended to substantially mask these disadvantages. For example, chemical stability is substantially improved by the glazes.

In the case of coatings on high-performance ceramics, however, the attempt is made to combine the advantageous properties of coating substances with those mechanical and thermal properties of the substrate material which suffice for the extreme stresses.

For example, coatings of various chemical elements and compounds are used and proven in technology which are applied to the substrate by CVD, PVD, plasma or other such techniques and also combinations of same. What is a disadvantage in these methods of application is that they work through the gaseous phase which causes the number of materials that can be used for the coating to be greatly limited. The coating thicknesses which can be achieved range from a few µm to about 25 µm and, due to the coating process, are very costly. With the methods referred to it is possible only to modify the surface properties. It is not possible, however, to substantially affect the structure of the surfaces. Moreover, the adhesiveness of the coatings depends on the process used. In coating by the plasma process the adhesion of the coating is accomplished only by adhesive forces, so that the duration of the bond is accordingly limited.

Other thermal and chemical coating methods have the disadvantage that the coating process affects the structure of the substrate material and its material properties can even be impaired. On account of the two-step method for the manufacture of a component as substrate followed by coating, tensions can be produce between the coating and the material which impair the adhesivity of the coating to the substrate, Sintering ceramic bodies of different porosity to one another is state of the art, but on account of problems at the boundary surface f the bodies and the internal tensions that occur no complex components can be made.

Ceramic bodies which consist entirely of an open-pored material are state of the art. But their mechanical strength is greatly reduced.

By the above-mentioned method, therefore, the production of a coating of defined thickness and pore structure on a closely sintered substrate of an inorganic material is not possible.

The invention is therefore addressed to the problem of preventing the known disadvantages in the production of a porous coating on a sintered body of an inorganic material, The solution of the problem is accomplished by means of a shaped body, as claimed in the first claim, and a method for the production of a body, especially one according to claims 1 to 15, as it is claimed in claim 16. Advantageous embodiments of the invention are claimed in the sub-claims.

The invention avoids the disadvantages of the state of the art in the production of a body with a porous coating on its surface by the fact that first a base body, the substrate, is shaped as a greenbody from an inorganic material, and a suspension of the same inorganic material of which the substrate consists, or of some other material, is applied to the substrate in its state as a greenbody. This suspension contains in addition to the inorganic material a pore-forming substance. Only after the application of the coating is a heat treatment of the substance and coating together performed by drying and sintering to produce a monolithic shaped body. The method for the production of the substrate is not different from the methods known in the state of the art.

The base body can be either free of pores, densely sintered, or also can contain pores. In the last case it also contains in its state as a greenbody, a percentage of a pore forming substance. Of course, the content of this substance is then such that the amount of pores per unit volume is always greater in the coating than in the substrate.

Suitable as inorganic materials for the base body, the substrate, are especially ceramic materials such as the known oxide ceramics, also silicates, phosphates, apatite and related materials, as well as nitrides, carbides and suicides. It is also possible to make bodies by the method of the invention with a porous surface coating from metals produced by powder metallurgy.

The same inorganic materials are suitable for the production of the coating which are suitable for the production of the base body. It is indeed advantageous if, in selecting an inorganic material for the coating which is not identical with the inorganic material of the base body, to assure that the material of the substrate and the material of the coating have nearly the same coefficients of expansion and the same great thermal stability in the temperature range to be used for the sintering of the body. This will prevent it from happening that, due to the different expansion of the various inorganic materials and to changes in the lattice structure or chemical composition, tensions especially in the boundary area between the two materials may lead to the separation or destruction of the coating, There is an advantageous effect on the thermal behavior of the body during the sintering process when the grain size of the material of the substrate and the grain size of the cover material are the same. If they are different, there is the danger, especially in the boundary area between the base body, the substrate and the coating, that tensions might occur which also might result in the separation or destruction of the coating.

To enable a porous coating to form on the base body—the substrate—the inorganic material to be used for the coating in a suitable grain size with a suitable liquid and a suitable pore forming substance are mixed to form a suspension and this suspension is applied in the necessary thickness to the greenbody. The preparation of a suspension of aninorganic material in a liquid adjusted to this material, allowing for shrinkage during heat treatment, drying and sintering, and from a substance appropriate to the size, shape an number of the pores, are known in the state of the art, for example in DE 44 42 810 A1, DE 44 32 477 C2 or the publication, "Einfluss von organischen Verbindungen auf keramische Massen" [influence of organic compounds on ceramic mixtures], W. Mann, Ber. DKG, 373 (1960), pp 11 to 22.

In the last-named publication a series of methods for the formation of pores is explained. Accordingly, there are the burn-out method, the solution method, the sublimation method, the evaporation method, the swelling method, the gassing method and the foaming method.

Suitable pore forming substances are especially organic substances, such as starches, cellulose or waxes, and natural and synthetic polymers which evaporate, turn to gas, are consumed or burn and thereby form the pores. The number of pores per unit volume, their size, that is their diameter, as well as their shape, can advantageously be determined through the selection of a suitable pore-forming substance. In the case of solid substances, the amount of particles, their size and their shape are the decisive factors. The shape of a solid pore forming substance can be, for example, spherical, globular, laminar or fiber-like.

As a rule the pore forming substances are converted during the heat treatment of the body to a gaseous phase which, when the gas escapes from the body, results in open pores, that is, the pores are joined together. As it can be learned from the last-named publication, there are also processes, such as gassing and foaming methods, in which the pores remain closed. The nature of the pores depends on the anticipated use of the body. Open pores are advantageous whenever liquids or gases are to pass through the body and, for example, additional substances are to be deposited in the pores. Bodies with closed pores are suitable, for example, for sound and thermal insulation as well as electrical insulation.

Porosity, i.e., the number of pores per unit volume, can be controlled by the amount of the pore forming substance added, or its concentration in the case of liquid substances, such that the porosity is approximately between 25% and 90%, preferably between about 25% and 70%. The pore size, pore diameter, depends in the case of solid substances, particularly on the particle size of the pore building substance and can be adjusted to sizes between about 1 μm and 1000 μm, preferably between 20 μm and 500 μm. It is required that the substances used do not undergo any change in volume during the burn-out or outgassing.

In an advantageous embodiment of the invention, when the coating is applied to the base body or substrate, while it is a greenbody, the moisture content of the suspension is adapted to the preliminary compression of the material of the substrate. The lower the preliminary compression of the substrate is and the higher its moisture content is, the more carefully must the moisture content of the suspension be adjusted so that the substrate will retain its shape and stability when the coating is applied. Moreover, the moisture content of substrate and suspension must be coordinated with one another so that, during the subsequent heat treatments the shrinkage of substrate and coating will be approximately the same, so that fissures, deformation or break-up of the coating will not occur while they are drying.

The coating materials as well as the pore-forming substances are suspended in water or other appropriate liquid which is known in the already-named state of the art, so that the suspension has a consistency suitable for the application process. Moreover, to produce a suspension, dispersants can be added with which a uniform distribution of the solids within the suspension is achieved. By adding organic or inorganic adjuvants the viscosity of the suspension can be controlled. By the addition of highly wetting liquid, the strength of the adhesion to the substrate in the green state can be increased.

What has been stated as advantageous process parameters for preparing the suspension for application to the substrate equally applies to the preparation of the substrate itself.

The process for applying the coating to the substrate can advantageously be adapted to the geometry and the shape of the surface of the substrate as well as the desired thickness of the coating. The coating can be applied to the entire surface of the substrate or else only to one or more portions thereof.

For complex surface structures as well as thin coatings of about 0.02 mm to about 2 mm, the immersion method is especially suitable. The immersion method also makes it possible to build up a coating in a number of immersion steps following one on the other up to the desired total thickness. After each immersion which builds up a coating in a certain thickness, this coating is first dried to a degree appropriate for the formation of the next coating before the next coating is made.

Especially on planar surfaces the suspension can also be brushed, and in the case of thick coatings it can be applied with a spatula. Spraying requires a sprayable suspension. Sprayed-on coatings have a rough surface which can be advantageous, for example, in the case of implants or catalysts. The coatings can also easily be applied successively by spraying. By means of the proposed methods coatings can be applied ranging from about 0.02 mm to 10 mm, preferably about 0.1 mm to 2 mm. By changing the properties of the features listed below, as well as the possible combination of these features, i.e., by different inorganic materials in substrate and coating, by different amounts of pores per unit of volume in the substrate and in the coating, by the pore size and pore shape, by the thickness of the coating, the arrangement of the coating on the surface of the substrate as well as the shape of the surface of the coating itself, a number of applications can be found for bodies according to the invention, of which a number of examples are listed herewith:

The bodies according to the invention can be used for example as implants in medical technology. Medical implants, for example socket inserts for hip joints, are made from high-purity aluminum oxide ceramic for the sake of good tolerability and biocompatibility as well as good wear characteristics. With a coating which consists also of aluminum oxide, $Al_2O_3$ in a thickness of a few tenths of a millimeter and with open pores with a diameter of about 200 μm to 400 μm, the bone tissue is given the possibility of growing onto or into the coating and a direct anchoring of the socket in the bone is possible. Instead of coating the socket as the base body with a porous aluminum oxide coating, it can also be coated with a coating of hydroxyl apatite or other calcium phosphate compounds in the same thickness and with the same pore structure. Hydroxyl apatite facilitates the growth of the bone tissue into the pores of the coating of the implant. Hydroxyl apatite can also additionally applied in a thin layer to the porous aluminum oxide coating.

The following examples indicate possible industrial applications. Onto a silicon nitride substrate, $Si_3N_4$, an additional coating of silicon nitride is applied so that then a very adherent, active coating with precursors can follow.

In process technology and in chemistry, porous coatings of silicon carbide, SiC, on substrates which are also made of silicon carbide, promote the evaporation of liquids due to the enlarged surfaces.

The shaped bodies according to the invention are also suitable as catalyst supports, The porous coating then serves on the highly refractory ceramic substances as support for the catalyst material. Such catalysts find application for example in motor vehicles and in the chemical industry. Also, the bodies according to the invention serve for lining containers, pipelines and troughs in metallurgy and in the chemical industry. For example, in the case of surfaces of foundry tools that come in contact with molten metals, for example, to protect them against corrosion, a porous coating of cordierite on nonporous cordierite or a porous coating of aluminum titanate on nonporous ammonium titanate is proposed. Thus the surface tension is increased against the molten metals and the wetting action is reduced.

The invention is explained with the aid of the following embodiments.

Figure 2:
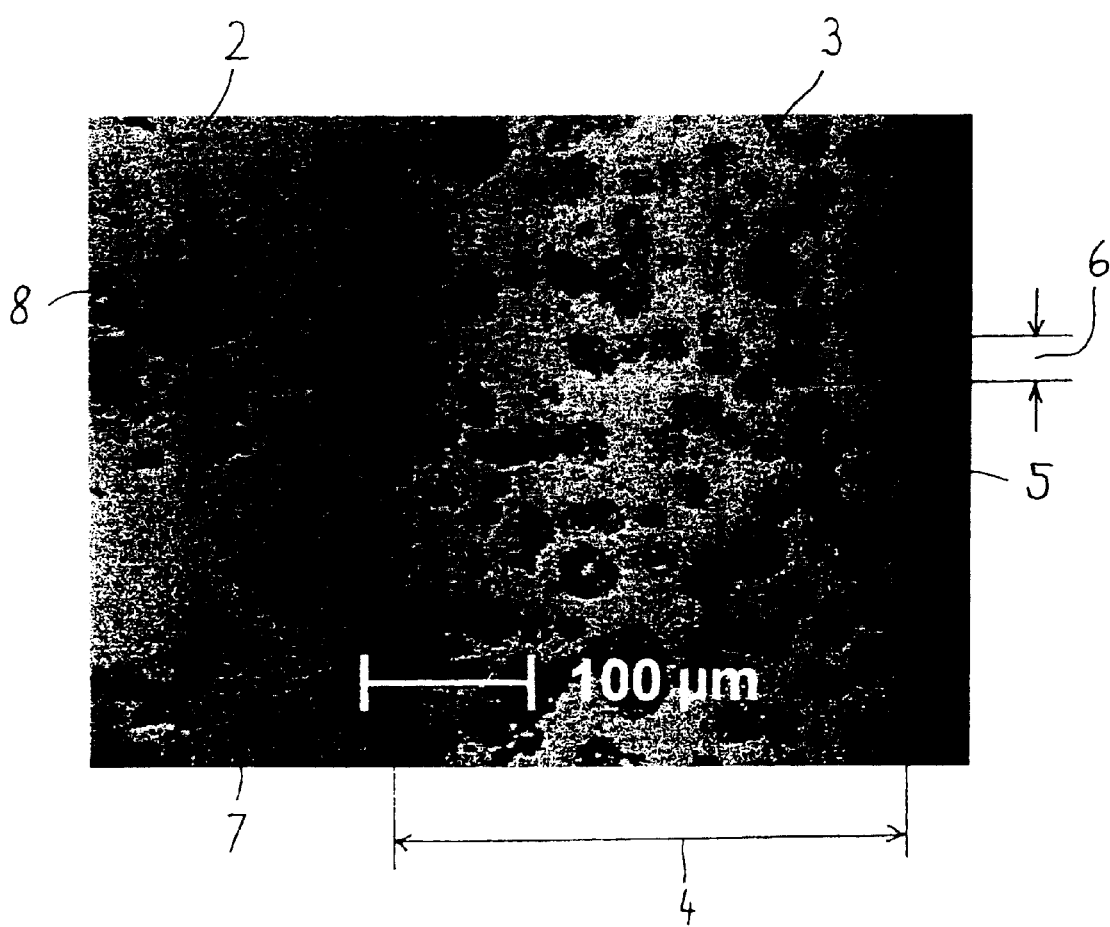
Figure 3:
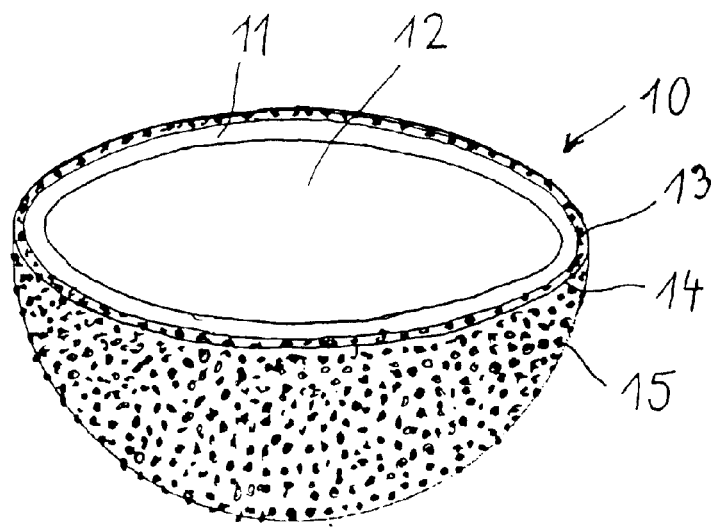
Figure 4:
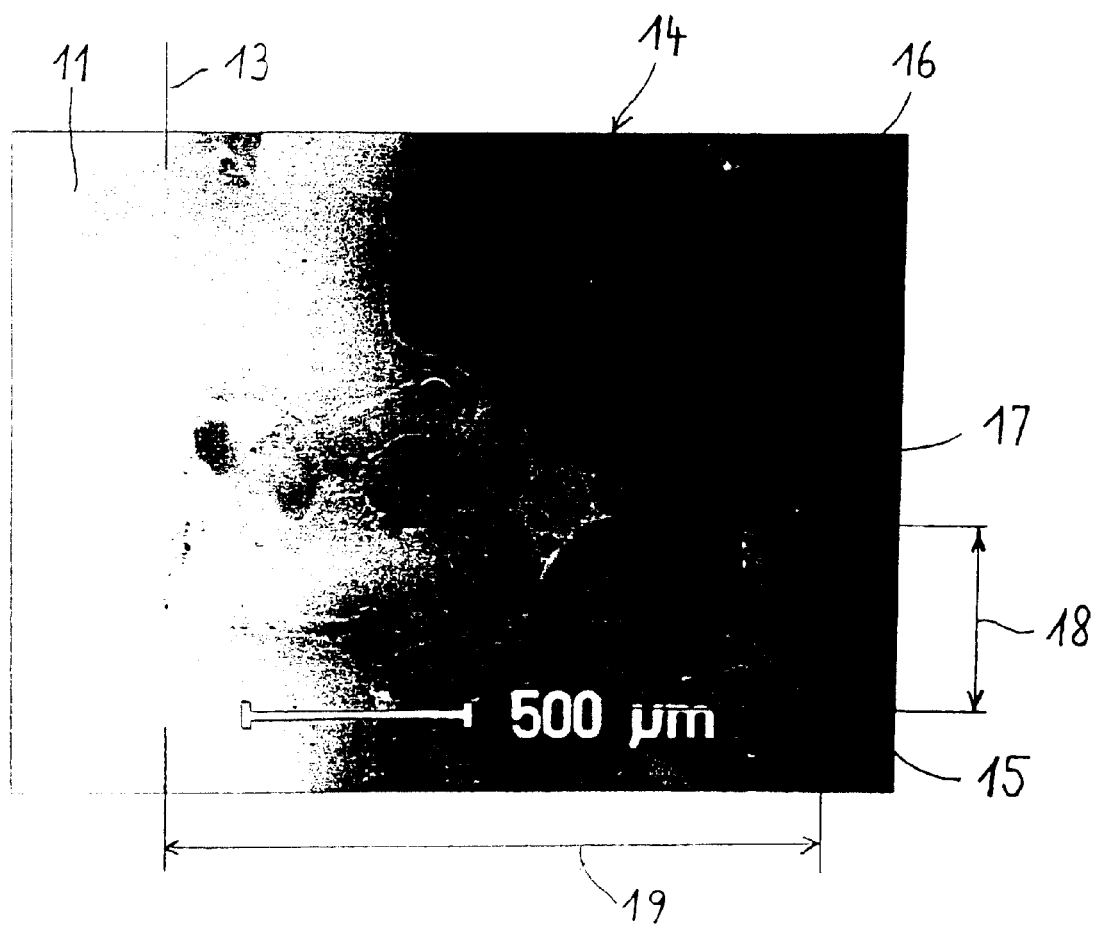

FIG. 1 shows a flat body with a porous coating,

FIG. 2 an enlarged microsection of the porous coating and the adjacent base body, FIG. 3 an insert cup of a hip joint endoprosthesis with a coating promoting the ingrowth of the bone tissue, and FIG. 4 an enlarged microsection of the porous coating and the contiguous material of the insert cup.

Now the production of a shaped body of silicon nitride, $Si_3N_4$, according to the invention will be described, as it is represented in FIG. 1 and identified by 1. By the process steps known in the state of the art, silicon nitride is prepared by dispersion in water with the addition of soluble binders, by grinding and spray drying to form a pressable dough. The granular product obtained by spray drying is pressed at an axial pressure of 2000 bar to form a square plate 1 with an edge length of 17 mm and a height of 7 mm. The embodiment is represented on an enlarged scale in FIG. 1. The density of the greenbody 2 is 1.9 g/cm, corresponding to 60% of the theoretical density of $Si_3N_4$.

A portion of the aqueous $Si_3N_4$ dispersion is separated prior to the spray drying. The solid content is about 60 wt.-% (weight percent). 15 wt.-% if a starch powder of a grain size between 20 µm and 50 µm is added to the dispersion. The thick dispersion thus prepared is brushed as coating 3 onto the pressed $Si_3N_4$ plate, the substrate 2. The water content of the applied dispersion is absorbed by the greenbody 2 and the applied coating 3 solidifies. By repeated brushing the thickness 4 of the coating 3 can be established as desired, for example up to 2 mm. The moisture content of the substrate 2 as the greenbody and of coating 3 is adapted one to the other such that tensions and cracking are avoided in the drying and in the firing that follows.

The substrates 2, the plate 1, provided with the coating 3, are dried like conventional greenbodies of silicon nitride, and sintered at the usual sintering temperature of up to 1800° C. The coating 3 sinters monolithically with the substrate 2. The burnt-out organic matter leaves open pores 5 behind.

FIG. 2 shows a section through the coating 3 on the plate 1 and the area of substrate 2 beneath it. The photograph shows a 200-times enlargement by a light microscope. The thickness of the porous coating 3 on the right amounts to about 0.3 mm, an approximately uniform distribution of coherent, spherical pores 5 of approximately equal size are clearly to be seen in the coating 3, and they have a diameter 6 of about 20 µm to 30 µm. The amount of pores per unit volume—the porosity—is about 35%.

The marginal layer 7 of the substrate 2 likewise has pores 8 which are somewhat larger and irregularly arranged than the pores of the porous coating 3. This effect, which is generally called "sinter skin" in connection with ceramic materials, has its cause in reactions between the surface and the sintering atmosphere. The marginal layer 7 in the present embodiment forms, for example, when silicon nitride is sintered in the presence of substances which as they decompose give off gases containing carbon and oxygen which react with the nitrogen and the silicon and likewise form gaseous phases, such as SiO and $N_2$. This has been the case in the sintering of the present embodiment, because the starch powder has decomposed. The gases which thus formed have reacted with the material of the marginal layer 7 to form pores. The porosity decreases inward from the surface of the substrate 2. The sinter skin can reach a thickness up to 3/10 mm.

While the so-called sinter skin is removed as a rule by grinding, because its porosity interferes with the otherwise intended purpose of sintered ceramics, it can even be regarded as desirable in the present case, because the pores are thereby opened all the way into the base body. In the case of the infiltration of these pores, for example, the result is the possibility of anchoring the porous coating firmly into the base body, the substrate 2, by means of the infiltrated materials.

In FIGS. 3 and 4 an embodiment from medical technology is represented. FIG. 3 shows a socket insert 10 of a hip joint endoprosthesis made of aluminum oxide, $Al_2O_3$, The socket insert 10 consists of the base body 11 with the slip surface 12 and the outer surface 13 on which a porous coating 14, also of aluminum oxide, has been applied. This porous coating 14 is intended to promote the ongrowth and ingrowth of the bone tissue. The coating 14 has uniformly distributed open pores 15.

The coating 14 is developed out of the material intended for the production of the socket insert. 15 wt.-% of a polyethylene wax with a grain size between 100 µm and 500 µm is added to this dispersion. The viscous dispersion thus prepared is spread onto the outer surface 13 of the base body 11, the procedure being as described in the previous embodiment.

FIG. 4 shows a light microscope photograph in a fifty-fold enlargement of a micrograph of the structure of the porous coating 14 and the adjoining base body 11 after sintering. Clearly seen is the base body 11 appearing to be pore-free, and its outer surface 13 as a boundary between base body 11 and porous coating 14. The specimen taken from a socket insert is embedded in a synthetic resin 16 appropriate for the production of photomicrographs. The embedding material 16 appears dark in the micrograph. It has filled the pores 15 and for this reason they can hardly be seen, especially in the transition to the surface 17 of the coating 14. The coating 14 has a thickness 19 of around 1.5 mm and a porosity of about 50%. It consists of the same material as that of the base body 11, i.e., $Al_2O_3$.

The round pores 15 of up to 400 µm diameter form a largely cohesive structure As it can be seen, the result is a very greatly fissured surface which advantageously promotes the ongrowth and ingrowth of bone tissue.

The invention claimed is:

1. A shaped body comprising a base body comprising a sintered shaped greenbody comprising a ceramic material and a porous coating comprising a ceramic material and a pore forming substance on at least a portion of the surface of the base body, wherein the base body and porous coating having a different number of pores per unit volume and the shaped body is monolithic; wherein after the shaped body is sintered the coating is monolithically sintered together with the substrate and wherein the substrate has a content of less than 1% of pores per unit volume, and wherein the substrate and the coating consist of different ceramic materials.

2. The shaped body according to claim 1, wherein the substrate is completely coated with said porous coating.

3. A shaped body comprising a base body comprising a sintered shaped greenbody ceramic material and a porous coating comprising a ceramic material and a pore forming substance on at least a portion of the surface of the base body, wherein the base body end porous coating having a different number of pores per unit volume and the shaped body is monolithic; wherein after the shaped body is sintered the coating is monolithically sintered together with the substrate and wherein the substrate has a content of less than 1% of pores per unit volume,
wherein the substrate is completely coated with said porous coating, and the grain size of the ceramic material of the substrate and the grain size of the ceramic material of the coating are different and wherein the substrate and coating comprise different ceramic materials.

4. The shaped body according to claim 1, wherein the ceramic material of the substrate and the ceramic material of the coating have coefficients of expansion of virtually equal magnitude and a virtually equal thermal stability in the temperature range which is necessary for the sintering of the greenbody.

5. A shaped body comprising a base body comprising a sintered shaped greenbody ceramic material and a porous coating comprising a ceramic material and a pore forming substance on at least a portion of the surface of the base body, wherein the base body and porous coating comprise different ceramic materials and have a different number of pores per unit volume and the shaped body is monolithic; wherein after the shaped body is sintered the coating is monolithically sintered together with the substrate and wherein the substrate has a content of less than 1% of pores per unit volume, wherein the grain size of the ceramic material of the substrate and the grain size of the ceramic material of the coating are the same.

6. The shaped body according to claim 1, wherein the thickness of the coating on the substrate is approximately between 0.02 mm and 10.

7. The shaped body according to claim 1, wherein the proportion of pores per unit volume in the coating is approximately between 25% and 90%.

8. The shaped body according to claim 1, wherein the diameter of the pores in the coating is approximately between 1 µm and 1000 µm.

9. The shaped body according to claim 1, wherein the shaped body is a medical implant.

10. The shaped body according to claim 1, wherein the shaped body is a component of a filter.

11. The shaped body according to claim 1, wherein the shaped body is component of a catalyst.

12. The shaped body according to claim 1, wherein the shaped body is component of a foundry tool.

13. The shaped body according to claim 1, wherein the shaped body is component of a cutting tool.

14. The shaped body according to claim 1, wherein the shaped body serves as a lining of containers, pipelines and troughs in metallurgy and in the chemical industry.

15. A method for the manufacture of a shaped body comprising
shaping a base body comprising at least one inorganic material to form a greenbody;
applying a coating comprising a suspension of a predetermined proportion of a pore forming substance and an inorganic material to at least a portion of a surface of the base body and subjecting the coated greenbody to a heat treatment to produce the monolithic sintered shaped body.

16. A method according to claim 15, wherein a pore-forming substance is admixed only to the material of the coating to be applied.

17. A method according to claim 15, wherein a coating comprising a different material is applied to the substrate than the one of which the substrate consists.

18. A method according to claim 16, wherein the greenbody is dried or sintered prior to application of the coating.

19. A method according to claim 16, wherein the moisture content of the suspension is adapted to the preliminary compression of the material of the substrate that is still in the green state.

20. A method according to claim 19, wherein the viscosity, the wetting and drying behavior and the adhesive strength of the suspension is adapted to the state of the material of the substrate that is still in the green state.

21. A method according to claim 15, wherein the application of the material of the coating is performed by dipping.

22. A method according to claim 15, wherein the application of the material of the coating is performed by brushing or troweling.

23. A method according to claim 15 wherein the application of the material of the coating is performed by spraying.

24. A method according to claim 21, wherein the coating is applied in several layers.

25. A method according to claim 15, wherein the coating is applied in a thickness at which the shrinkage caused by the heat treatments is allowed for.

26. A method according to claim 15, wherein the material of the coating is applied in a thickness of about 0.02 mm to about 10.

27. A method according to claim 15, wherein the substance forming the pores is admixed to the material of the coating in such an amount or concentration that when the shaped body is sintered the specified proportion of pores per unit of volume is reached, which is approximately between 25% and 90%.

28. A method according to claim 15, wherein the particle size of a solid substance forming the pores is adapted to the desired number of pores to be produced, which is approximately between 1 µm and 1000 µm.

29. A shaped body according to claim 2, wherein the substrate has a content of less than 1% of pores per unit volume.

30. The shaped body according to claim 11, wherein a coating of another material is applied to the substrate than the one of which the substrate consists.

31. The shaped body prepared by the method of claim 15.

32. The shaped body according to claim 6, wherein the thickness of the coating on the substrate is approximately between 0.1 mm and 2 mm.

33. The shaped body according to claim 7, wherein the proportion of pores per unit volume in the coating is approximately between 25% and 70%.

34. A shaped body comprising a base body comprising a sintered shaped greenbody ceramic material and a porous coating comprising a ceramic material and a pore forming substance on at least a portion of the surface of the base body, wherein the base body and porous coating comprise different ceramic materials and have a different number of pores per unit volume and the shaped body is monolithic; wherein after the shaped body is sintered the coating is monolithically sintered together with the substrate and wherein the substrate has a content of less than 1% of pores per unit volume, wherein the diameter of the pores in the coating is approximately between 20 µm and 500 µm.

35. A method according to claim 26, wherein the material of the coating is applied in a thickness of about between 0.1 mm and 2 mm.

36. A method according to claim 27, wherein the substance forming the pores is admixed to the material of the coating in such an amount or concentration that when the shaped body is sintered the specified proportion of pores per unit of volume is reached, which, is approximately between 25% and 70%.

37. A method according to claim 28, wherein the particle size of the solid substance forming the pores is adapted to the desired number of pores to be produced, which is approximately between 20 µm and 500 µm.

38. The shaped body of claim 31, wherein said inorganic material is a ceramic.

39. The shaped body of claim 31, wherein the base body is monolithic.

40. The shaped body of claim 38, wherein the base body is monolithic.

41. The shaped body according to claim 6, wherein the proportion of pores per unit volume in the coating is approximately between 25% and 90%.

42. A shaped body comprising a single base body comprising a sintered shaped greenbody ceramic material and a porous coating comprising a ceramic material and a pore forming substance on at least a portion of the surface of the base body, wherein the base body and porous coating having a different number of pores per unit volume and the shaped body is monolithic.

43. The shaped body of claim 1, wherein base body has a content of less than 1% of pores per unit volume.

44. The method of claim 15, wherein said heat treatment is sintering.

45. A shaped body comprising:
a sintered shaped greenbody ceramic;
a porous coating comprising a ceramic on at least a portion of a surface of said base body; and
a porous marginal layer between said base body and said porous coating.

46. A shaped greenbody having at least one surface coated with a suspension comprising a ceramic and a pore former.

47. A method comprising applying a suspension comprising a ceramic and a pore former to at least a portion of a surface of a shaped greenbody.

48. A monolithic shaped body comprising a base body comprising a sintered shaped greenbody comprising a ceramic material and a porous coating on at least a portion of the surface of the base body, wherein the base body and porous coating have a different number of pores per unit volume; and wherein the porous coating is formed by applying a suspension comprising a ceramic and a pore forming agent to a green body ceramic and monolithically sintering the coated green body to form the monolithic shaped body and wherein the substrate and the coating comprise different ceramic materials.

49. The shaped body according to claim 48, wherein the substrate is completely coated with said porous coating.

50. The shaped body according to claim 49, wherein the grain size of the ceramic material of the substrate and the grain size of the ceramic material of the coating are the same.

51. The shaped body according to claim 48, wherein the ceramic material of the substrate and the ceramic material of the coating have coefficients of expansion of virtually equal magnitude and a virtually equal thermal stability in the temperature range which is necessary for the sintering of the greenbody.

52. The shaped body according to claim 48, wherein the grain size of the ceramic material of the substrate and the grain size of the ceramic material of the coating are the same.

53. The shaped body according to claim 48, wherein the thickness of the coating on the substrate is approximately between 0.02 mm and 10 mm.

54. The shaped body according to claim 48, wherein the proportion of pores per unit volume in the coating is approximately between 25% and 90%.

55. The shaped body according to claim 48, wherein the diameter of the pores is approximately between 1 µm and 1000 µm.

56. The shaped body according to claim 48, wherein the shaped body is a medical implant.

57. The shaped body according to claim 48, wherein the shaped body is a component of a filter.

58. The shaped body according to claim 48, wherein the shaped body is component of a catalyst.

59. The shaped body according to claim 48, wherein the shaped body is component of a foundry tool.

60. The shaped body according to claim 48, wherein the shaped body is component of a cutting tool.

61. The shaped body according to claim 48, wherein the shaped body serves as a lining of containers, pipelines and troughs in metallurgy and in the chemical industry.

62. A method according to claim 16, wherein the greenbody is dried prior to application of the coating.

63. A shaped body comprising a base body comprising a sintered shaped greenbody comprising a ceramic material and a porous coating comprising a ceramic material and a pore forming substance on at least a portion of the surface of the base body, wherein the base body and porous coating having a different number of pores per unit volume and comprise different ceramics; wherein the shaped body is monolithic; wherein after the shaped body is sintered the coating is monolithically sintered together with the substrate and wherein the substrate has a content of less than 1% of pores per unit volume.

64. A sintered shaped body prepared by the process of:
forming a green body comprising a first ceramic material;
applying a coating comprising a second ceramic material and a pore forming substance to the green body to form an unsintered shaped body;
sintering the unsintered shaped body to form the sintered shaped body, wherein the coating is porous and wherein the green body, after sintering, forms a substrate having less that 1% pores per unit volume and wherein the first and second ceramic material are different.

65. The sintered body of claim 64, wherein the first and second ceramic material have coefficients of expansion of virtually equal magnitude.

66. The sintered body of claim 65, wherein the first and second ceramics have virtually equal thermal stability in the temperature range at which the sintering occurs.

67. A shaped body comprising a sintered greenbody comprising a first ceramic and porous coating comprising a second ceramic that have been sintered together, wherein the sintered greenbody has a content of less than 1% of pores per unit volume and the coating and the sintered greenbody are monolithic wherein the first and second ceramics are different.

68. The method of claim 47, further comprising sintering the greenbody to which the suspension has been applied to form a sintered shaped body comprising a porous coating formed from the sintered suspension and a sintered greenbody.

69. The method of claim 68, wherein the coating and sintered greenbody are monolithic.

70. The method of claim 69, wherein the porous coating has a porosity, but said porosity is less than 1% pores per unit volume.

71. The shaped body according to claim 63, wherein the coefficient of expansion of the shaped body and the coefficient of expansion of the coating are different.

* * * * *